United States Patent [19]
Angell

[11] Patent Number: 5,861,028
[45] Date of Patent: Jan. 19, 1999

[54] NATURAL TISSUE HEART VALVE AND STENT PROSTHESIS AND METHOD FOR MAKING THE SAME

[76] Inventor: William W. Angell, 4931 New Providence Ave., Tampa, Fla. 33629

[21] Appl. No.: 711,067

[22] Filed: Sep. 9, 1996

Related U.S. Application Data

[60] Provisional application No. 60/009,611 Jan. 4, 1996.
[51] Int. Cl.⁶ ..................................................... A61F 2/24
[52] U.S. Cl. ............................................... 623/2; 623/900
[58] Field of Search ......................................... 623/2, 900

[56] References Cited

U.S. PATENT DOCUMENTS

| | | | |
|---|---|---|---|
| 3,570,014 | 3/1971 | Hancock | 3/1 |
| 3,739,402 | 6/1973 | Cooley et al. | 3/1 |
| 3,983,581 | 10/1976 | Angell et al. | 3/1.5 |
| 4,035,849 | 7/1977 | Angell et al. | 3/1.5 |
| 4,042,979 | 8/1977 | Angell | 3/1.5 |
| 4,079,468 | 3/1978 | Liotta et al. | 3/1.5 |
| 4,172,295 | 10/1979 | Batten | 623/2 |
| 4,247,292 | 1/1981 | Angell | 8/94.11 |
| 4,259,753 | 4/1981 | Liotta et al. | 3/1.5 |
| 4,349,498 | 9/1982 | Ellis et al. | 264/81 |
| 4,350,492 | 9/1982 | Wright et al. | 8/94.11 |
| 4,441,216 | 4/1984 | Ionescu et al. | 3/1.5 |
| 4,477,930 | 10/1984 | Totten et al. | 3/1.5 |
| 4,624,822 | 11/1986 | Arru et al. | 623/2 |
| 4,626,255 | 12/1986 | Reichart et al. | 623/2 |
| 4,629,459 | 12/1986 | Ionescu et al. | 623/2 |
| 4,692,164 | 9/1987 | Dzemeshkevich et al. | 623/2 |
| 4,725,274 | 2/1988 | Lane et al. | 623/2 |
| 4,759,758 | 7/1988 | Gabbay | 623/2 |
| 4,769,032 | 9/1988 | Steinberg | 623/2 |
| 4,816,029 | 3/1989 | Penny, III et al. | 623/2 |
| 4,851,000 | 7/1989 | Gupta | 623/2 |
| 5,024,232 | 6/1991 | Smid et al. | 128/654 |
| 5,032,128 | 7/1991 | Alonso | 623/2 |
| 5,156,621 | 10/1992 | Navia et al. | 623/2 |
| 5,336,258 | 8/1994 | Quintero et al. | 623/2 |
| 5,449,384 | 9/1995 | Johnson | 623/2 |
| 5,549,665 | 8/1996 | Vesely et al. | 623/2 |
| 5,549,666 | 8/1996 | Hata et al. | 623/2 |
| 5,562,729 | 10/1996 | Purdy et al. | 623/2 |
| 5,584,879 | 12/1996 | Reimold et al. | 623/2 |
| 5,628,791 | 5/1997 | Bokros et al. | 623/2 |

FOREIGN PATENT DOCUMENTS

| | | | |
|---|---|---|---|
| 1116-573-A | 1/1983 | U.S.S.R. | 623/2 |
| 2 206 395 | 1/1989 | United Kingdom | 623/2 |
| 83/00617 | 3/1983 | WIPO | 623/2 |

*Primary Examiner*—Michael J. Milano
*Assistant Examiner*—Tram A. Nguyen
*Attorney, Agent, or Firm*—Tarolli, Sundheim, Covell, Tummino & Szabo

[57] ABSTRACT

A composite natural tissue heart valve prosthesis which may be mounted in a cloth-covered, generally anatomical stent is disclosed. The prosthesis includes three adjacent tanned heart valve leaflets of generally similar size, shape and symmetry that are attached to adjacent leaflets along their respective valve wall side edges such that there is substantial coaptation between said cusps.

14 Claims, 7 Drawing Sheets

Fig. 17

NATURAL TISSUE HEART VALVE AND STENT PROSTHESIS AND METHOD FOR MAKING THE SAME

RELATED APPLICATION

This application claims the benefit of U.S. Provisional Patent Application No. 60/009,611 filed Jan. 4, 1996.

BACKGROUND OF THE INVENTION

1. Field of the Invention

The present invention generally relates to a heart valve apparatus and method of making the heart valve apparatus. More particularly, the present invention relates to an improved heart valve prosthesis of natural tissue cardiac valves that have been properly fixed in a solution and that may be mounted to an appropriate stent structure prior to implantation into the recipient.

2. Background of the Invention

Figure 1:
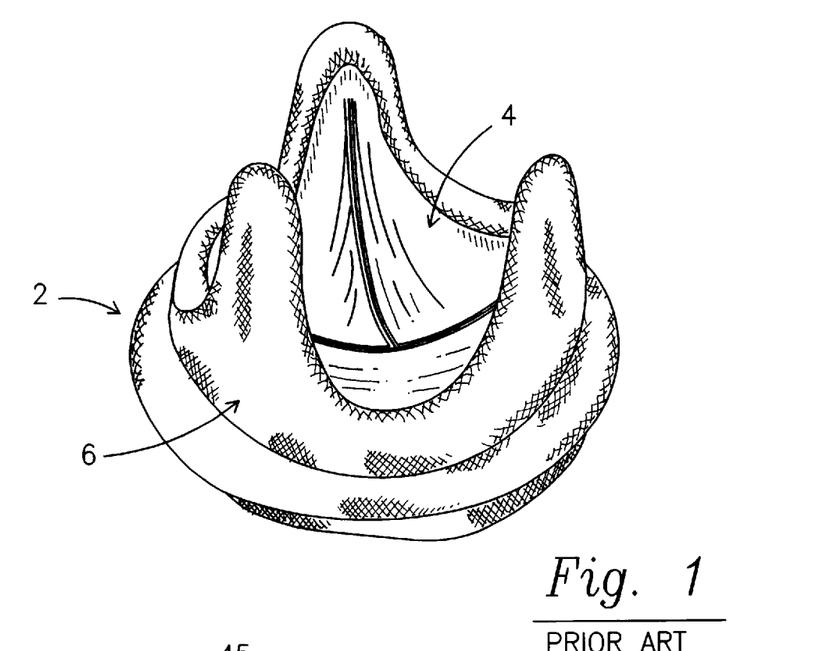
FIG. 1 is a perspective view of a prior art, natural tissue heart valve prosthesis.

It is well known to utilize mechanical heart valves, such as the ball check valve, and natural tissue cardiac valves to replace defective aortic and mitral valves in human patients. Referring to the natural tissue heart valves, porcine valves typically are utilized for implantation in humans, because they are very similar to human valves of appropriate size and generally are easy to procure. Prior art teaches the concept of removing an aortic heart valve from a pig, treating it with a glutaraldehyde solution and mounting it into a stent, which may then be implanted into a patient for a heart valve replacement. FIG. 1 illustrates such a prior art heart valve prosthesis, generally indicated as 2, that includes a porcine cardiac valve 4 with a conventional stent construction 6, such as described and disclosed in U.S. Pat. No. 3,983,581 and U.S. Pat. No. 4,035,849 both owned by William W. Angell, the inventor of the present invention.

While anatomically configured, natural tissue heart valve prostheses are well known in the art. Conventional valves often are unable to achieve a completely adequate level of coaptation between the leaflets. In addition, due to the configuration of such heart valve prostheses, there tends to be a significant amount of abrasion between the leaflets of the porcine valve and the conventional stent structures, which generally further decreases the longevity of the valve apparatus. Conventional stent structures are generally formed of a relatively rigid material that tends to be inflexible and difficult to manage by a surgeon during the implant procedure.

Conventional prostheses are typically constructed with a ring of radio-opaque material affixed prosthesis within an implantation flange circumferentially positioned proximal the inflow side of the valve. While the addition of such material, which may be viewed through fluoroscopy, may be beneficial during the post-implantation monitoring of the valve, it generally increases the outer diameter of the entire valve prosthesis and, thus, reduces the inner diameter to outer diameter ratio. U.S. Pat. No. 5,156,621 to Jose A. Navia discloses an unstented heart valve prosthesis that includes a suture ring having a continuous annular cord at the inflow side for implantation and a layer of a textile material covering the exterior of the entire structure. U.S. Pat. No. 4,759,758 to Gabbay discloses a heart valve prosthesis that includes a generally right-circular, cylindrical stent in which a single cusp formed of double over pericardium is mounted. The exterior of the Gabbay prosthesis is completely covered with a biological tissue layer, such as pericardium. A study of this and other such prior art heart valve prostheses readily leads one to the conclusion that such prior art generally fails to completely address the needs of a heart valve prosthesis.

SUMMARY OF THE INVENTION

In view of the foregoing, it is desired to provide an improved natural tissue, heart valve prosthesis that may provide an improved level of coaptation between the leaflets. It is also desired to provide a substantially symmetrical heart valve prosthesis that may operate substantially efficiently. It is still further desired to provide a natural tissue heart valve prosthesis that has an increased inner diameter to outer diameter ratio generally resulting in an improved flow orifice and improved hemodynamics. It is also desired to provide a heart valve prosthesis of substantially anatomical configuration.

To achieve these and other objects that will become apparent, the present invention provides a composite natural tissue heart valve prosthesis primarily intended for replacing a patient's defective heart valve. The prosthesis includes three adjacent tanned heart valve leaflets of generally similar size, shape and symmetry, with each valve leaflet including a valve wall and a cusp that is attached to and extends from leaflet valve wall proximal its respective inflow end. Each said leaflet valve wall has an inflow end, an outflow end and a pair of generally opposed side edges extending between its inflow and outflow ends. Each leaflet is attached to its adjacent pair of leaflets along at least a portion of its respectively adjacent valve wall side edges such that there is substantial coaptation between said cusps. In a preferred embodiment of the present invention, the composite heart valve prosthesis may suitably be attached within an appropriate stent structure.

BRIEF DESCRIPTION OF THE DRAWINGS

Preferred embodiments of the present invention will be described in detail in respect to the drawings in which.

DETAILED DESCRIPTION OF THE PREFERRED EMBODIMENT

Prior to the assembly of the heart valve prosthesis of the present invention, appropriate porcine valves that have no substantial anatomic abnormalities as well as no significant holes in the leaflets or cusps of the valve should be selected. The size of the porcine valve procured will generally depend upon the respective age of the heart valve donor animals. Consequently, donors are appropriately selected in order to provide cardiac valves having an outside diameter typically ranging from about 17 to about 33 mm.

Figure 2:
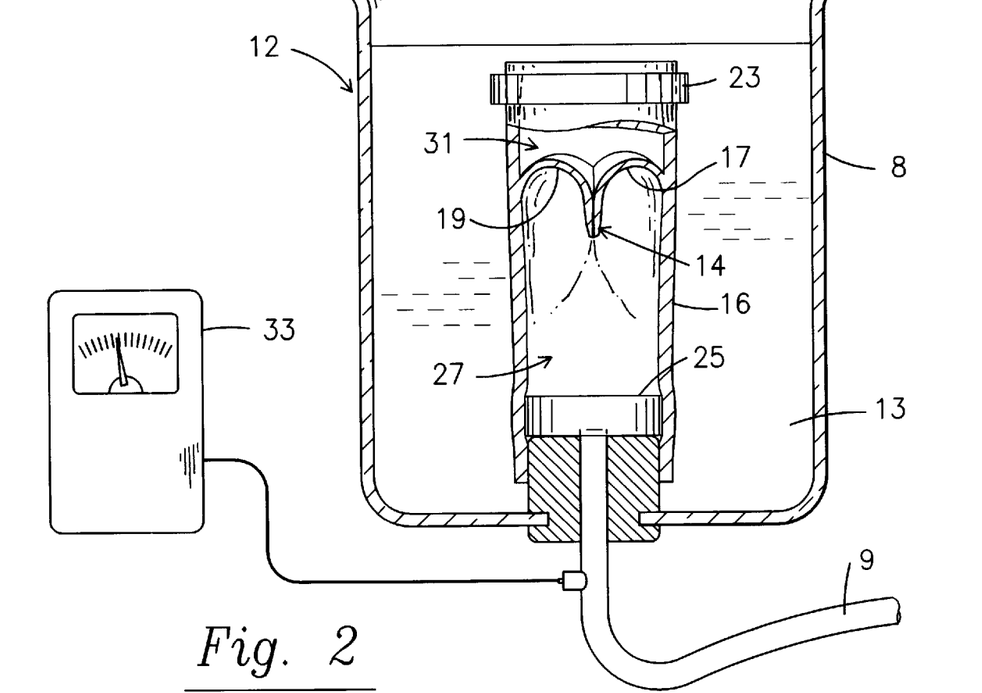
FIG. 2 is a schematic representation of a preferred fixation environment, partially in section, for fixing a natural tissue heart valve in accordance with the present invention.

Once an appropriate valve has been selected, it preferably undergoes an appropriate fixation process to improve the tensile properties of the valves as well as improve its biocompatibility by decreasing tissue reactivity with the heart valve recipient. This fixation process, shown in the schematic representation of FIG. 2, generally includes tanning the valve 14 in a container 8 having a predetermined glutaraldehyde solution 13 at a substantially constant temperature with a predetermined pressure being applied to the outflow end, generally indicated as 27, of the valve 14. While FIG. 2 shows a single porcine valve 14 undergoing appropriate fixation, it is to be understood that there will typically be a plurality of such valves being fixed at a given time. A suitable fixation environment 12 may include a 0.3 to 0.5 glutaraldehyde solution at a temperature ranging between 15° C. and 25° C. with a pressure between 0 and 4 mm Hg being applied at the outflow side of the valve. A more preferred fixation environment includes approximately a 0.35 glutaraldehyde solution at about 20° C. for at least 24 hours with about 2 mm Hg of pressure differential applied at the outflow side of the valve to assist in fixing the desired coaptation of the valve leaflets. After the initial tanning process, the valve may remain in the glutaraldehyde solution until it is required for inclusion in a heart valve prosthesis.

As shown in the schematic representation of FIG. 2, a preferred fixation process may include fitting a porcine aortic wall 16 that includes a valve, generally indicated as 14, with ring-like external and internal stents 23 and 25, respectively, mounted, with or without ligation, within the porcine aortic wall 16 proximal the outflow end 27 of the valve 14. The internal plug or stent 25 generally provides an attachment site to which appropriate pressure may be applied in order to maintain the valve 14 in a substantially closed position and achieve a desired coaptation between the cusps 17, 18 and 19. The pressure may be applied to the outflow end 27 by a conventional source (not shown) through an appropriate interface, such as tube 9, and may be monitored by a standard pressure gauge 33 to ensure that the pressure differential between the outflow end 27 of valve 14 and the surrounding solution 13 remains at a preferred level. In addition, ring shaped external and internal stents 23 may also be mounted to the inflow side, generally indicated as 31, of the valve 14 during the fixation process to maintain a preferred substantially circular shape as well as to promote the desired coaptation, suitably about 2 mm to about 4 mm of generally axial engagement, between the cusps 17, 18 and 19. The external and internal stents 23 and 25 typically are positioned circumferentially with respect to the external and internal circumferences of the aortic wall 16 of valve 14 proximal the inflow and 31 of the valve 14. Typically, the plug 25 and the internal and external stents 23, respectively, employed during fixation are selected to correspond to the size of the particular porcine valve 14 that is to be tanned and to the shape of the stent.

Figure 3:
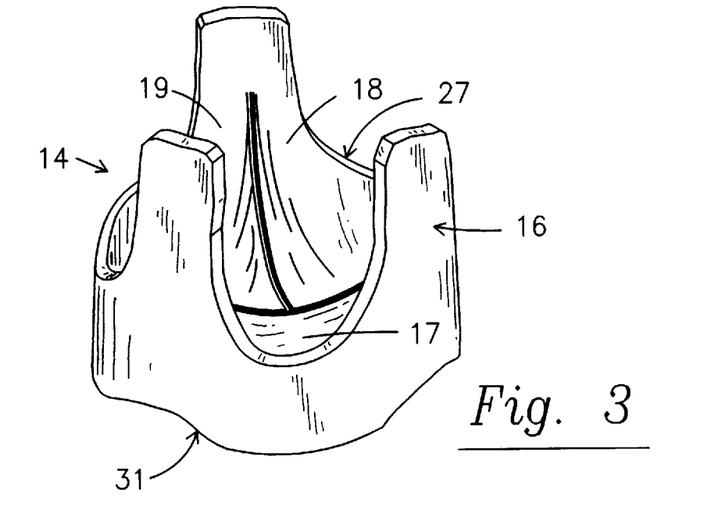
FIG. 3 is a perspective view of a preferred embodiment of a trimmed natural tissue heart valve in accordance with the present invention.

After the porcine valve 14 undergoes the fixation process, it may be appropriately trimmed for inclusion into a heart valve prosthesis, as shown in the premounted valve of FIG. 3, and typically includes cutting generally along the contour of the attachment of the cusps to the valve wall proximal the inflow and outflow ends 31 and 27, respectively, of the aortic valve 14. The fixed porcine valve 14 includes a generally cylindrical valve wall 16, an inflow end, an outflow end and three cusps 17, 18 and 19 that are integrally attached adjacent the inflow end of the valve 14 and extend along a portion of the valve wall 16. Along the outflow rail proximal each cusp 17, 18 and 19, a portion of the valve wall 16 may be removed to define three radially spaced posts with sinuses formed between each adjacent cusp 17, 18 and 19.

Figure 4:
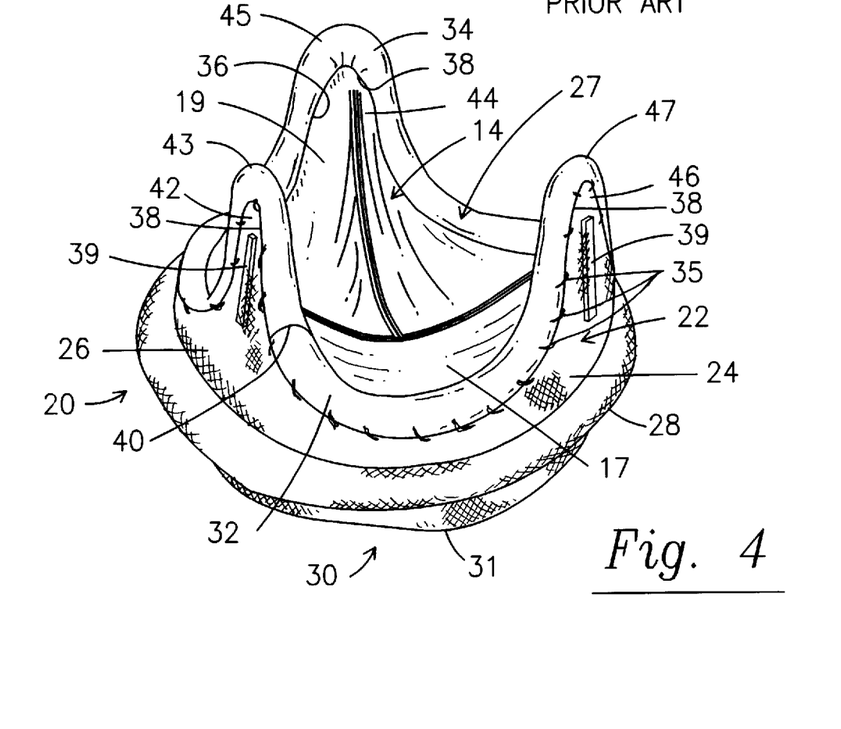
FIG. 4 is a perspective view of a preferred embodiment of a natural tissue heart valve prosthesis in accordance with the present invention.

FIG. 4 illustrates a preferred embodiment of a heart valve prosthesis, generally indicated as 20, that includes the trimmed porcine valve 14 of FIG. 3 mounted or attached within in a conventional stent, generally indicated as 22. Suitable stent structures include those disclosed in U.S. Pat. No. 3,983,581 and U.S. Pat. No. 4,035,849 both owned by William W. Angell, the inventor of the present invention as well as other structures well known in the art. Such stents 22 are preferably formed of thermoplastic materials, such as the material known commercially as Delrin, and may be manufactured, suitably by injection molding, in various sizes and shapes. For the preferred embodiment illustrated in FIG. 4 such stent structures 22 typically include at least, and preferably, three asymmetrically radially spaced and elongated stent posts 42, 44 and 46 extending from the annular base portion 24 that correspond generally to the anatomy of the heart valves such as shown in FIG. 3. Preferably, the stent posts 42, 44 and 46 are radially spaced apart along the outflow end of base portion to generally correspond to the radial positioning of the individual cusps of the heart valve 14. Such stent 22 also includes an inflow end 30, an outflow end 32, an interior and an exterior. At least a portion, although preferably the entire stent structure 22 is generally covered with a nonabsorbent textile or fabric cover 26, such as by sewing an open mesh Dacron polymer cloth or an equivalent material over the internal and external surfaces of the stent 22. Preferably, the valve 14 is attached, such as by sutures, within the stent structure 22 such that the inflow end of the valve 14 is positioned adjacent the inflow end of the stent with the outflow end of the valve positioned proximal and preferably conforming to the configuration of the stent posts.

Figure 5:
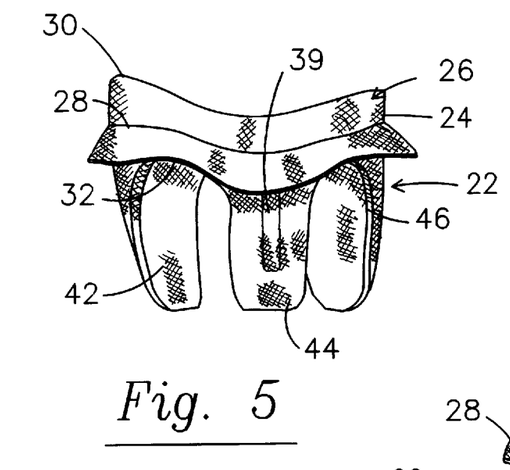
FIG. 5 is a side elevation of a preferred embodiment of a stent configured for a mitral valve heart prosthesis.

A generally annular implantation flange 28 may be attached to and circumscribe the exterior of the stent base 24 intermediate the inflow end 30 and the outflow end 32 of the stent. The flange 28 is suitably formed by sewing the flange 28 in the Dacron covering 26 that surrounds the stent 22. Preferably, the flange 28 includes an additional ring of Dacron material interposed between the top and bottom portions of the flange 28, such as by sewing, and may suitably be ironed prior to implantation to form a substantially flat ring-like structure circumscribing the stent base 24. As shown in FIGS. 4 and 5, the positioning of the implantation flange 28 will typically depend upon whether the porcine heart valve 20 will be implanted as a mitral valve, shown in FIG. 4, or an aortic valve, shown in FIG. 5. The implantation flange 28 for the aortic valve of FIG. 5 is preferably positioned generally adjacent to the inflow or ventricular edge 30 of the stent base portion 24, and the implantation flange 28 in the mitral valve shown in FIG. 4 is positioned substantially adjacent the outflow or aortic edge 32 of stent base 24.

Appropriate radio-opaque markers 39, which may suitably be formed of barium, silicone, a metal foil or other suitable materials known in the art preferably are positioned substantially longitudinally along at least one, although preferably each of the stent posts 42, 44 and 46 beneath the Dacron covering 26. By positioning the markers 39 along the stent posts 42, 44 and 46 rather than conventionally within the implantation flange 28, the inner diameter to outer diameter ratio of the valve will generally increase, resulting in an improved flow orifice and, consequently, improved blood flow through the implanted prosthesis.

Once an aortic porcine valve 14 has been mounted appropriately to the Dacron covered stent 22, a pericardium strip 34 having first and second ends, which may suitably be equine or porcine pericardium or other suitable generally smooth biocompatible material is attached, such as by suture 35, to at least a portion of the textile material of the outflow end 32 of the prosthesis 20. Preferably the strip 34 is attached along the outflow rails 36 of the stent 22 and the free margins 38 of the valve that are proximal the outflow ends of the respective stent posts 43, 45 and 47 and generally intermediate the posts beyond the attachment of the cusps to the valve wall 16. The pericardium strip 34 provides a natural tissue material for the valve leaflets to open against, which tissue is smoother than woven Dacron and, thus, generally inhibits the abrasion that typically occurs between the valve leaflets and the Dacron covering 26 as the leaflets permit the flow of blood. Preferably, the tanned strip of pericardium 34 is affixed to the heart valve prosthesis 20 such that its visceral, or smooth, side is exposed, and it may be tanned in a suitable glutaraldehyde solution. In addition, the strip 34 also tends to improve the compatibility between the heart valve prosthesis 20 and the valve recipient. The butt seam 40 of the pericardium strip 34 is preferably positioned along the side of one of the stent posts intermediate the post tip 43 and the stent base portion 24, with the two ends of the pericardium strip 34 seamed together end to end with substantially no overlap to define seam 40. In a relatively small sized valve prosthesis (not shown), the pericardium bias may be omitted with a continuous aortic margin stitch securing the aortic wall of the valve 14 to the outflow stent rails.

Once the heart valve prosthesis 20 has been assembled as set forth above, it preferably may be attached to an appropriate valve holder, such as illustrated in FIGS. 6 through 10, that may vary in construction depending upon whether the valve prosthesis is intended to replace an aortic valve or a mitral valve. Such holders may be injection molded and formed of a generally resilient material such as the commercially available Delrin. In general, the valve holders of FIGS. 7 through 11 maintain the valve prosthesis in a preferable configuration during storage as well as facilitate the implantation procedure by the surgeon.

Figure 7:
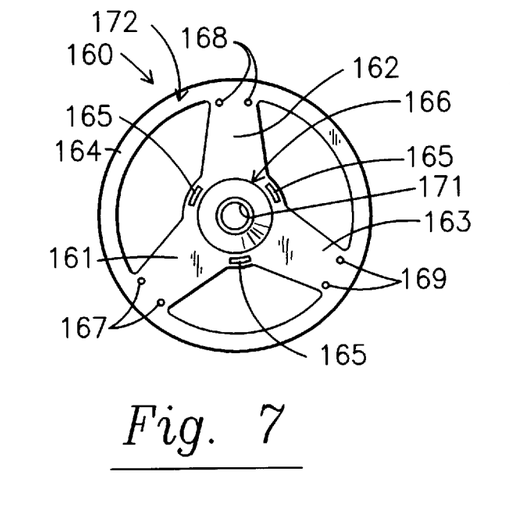
FIG. 7 is a top view of a preferred embodiment of an atrioventricular valve holder in accordance with the present invention.
Figures 8, 9, 10:
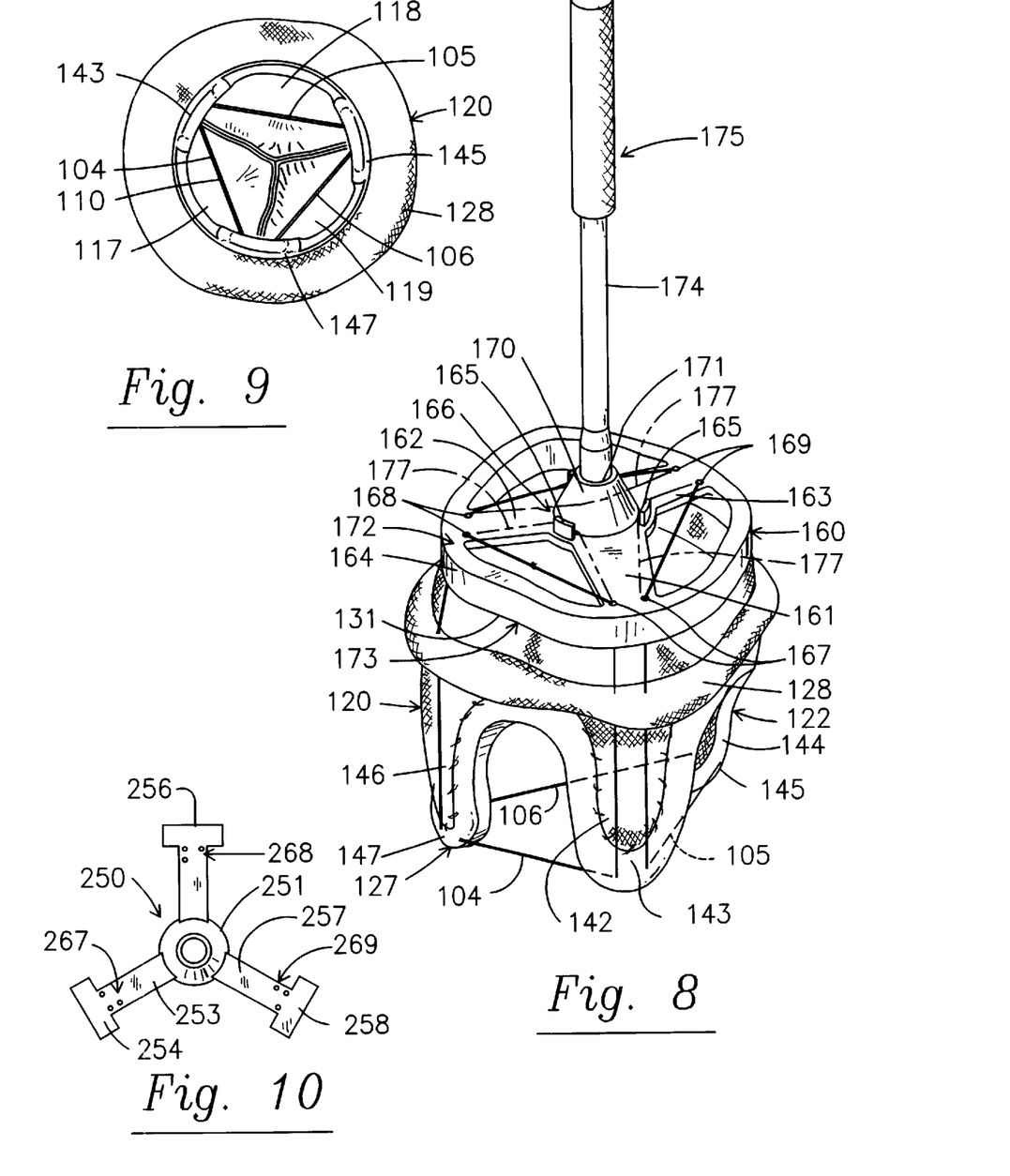
FIG. 8 is a perspective view of a preferred embodiment of the valve holder of FIG. 6 attached to a heart valve prosthesis with an appropriate attachment tool attached to the valve holder in accordance with the present invention.
FIG. 9 is the heart valve prosthesis of FIG. 8 viewed from the outflow side of the valve prosthesis.
FIG. 10 is a top view of a preferred embodiment of an aortic valve holder in accordance with the present invention.

FIGS. 7, 8 and 9 illustrate an atrioventricular valve holder 160 that is attachable to a heart valve prosthesis, generally indicated as 120 in FIG. 9, which may be configured for mitral valve replacement, at the inflow side 131 of the valve prosthesis 120. It will be understood that the valve holder 160 is well suited for, but not limited to, such mitral valve replacement. For simplification of illustration, reference numbers in the view of FIG. 8 that correspond to parallel components of the heart valve prosthesis 20 of FIG. 4 have been increased by adding a factor of 100.

The atrioventricular valve holder 160, having an upper side, generally indicated as 172, and a lower side, generally indicated as 173, preferably includes at least three spokes 161, 162, and 163 that attach to and extend between an annular ring 164 having two sides and an inner central base portion 166 having a central axis. Of course, a substantially solid member extending between base 166 and ring 164 may suffice in place of the individual spokes 161, 162 and 163. At least one hole, although preferably 2 or more holes 167, 168 and 169 are bored through each respective spoke 161, 162 and 163 proximal the attachment, or juncture, of the annular ring 164 and the spokes 161, 162 and 163. The preferred embodiment of the base 166 further includes a holder attachment 170 which is illustrated as a generally hollow cylinder extending generally upwardly from a generally planar surface of the base 166 that generally surrounds the holder attachment 170. The holder attachment 170 suitably includes an aperture 171 formed through at least a portion of the base 166 generally along the axis of the valve holder 160, with the holder attachment 170 being dimensioned and configured for receiving a tool, generally indicated as 175 in FIG. 8. The valve holder 160 preferably also includes at least one, although preferably a plurality of projections or suture tabs 165 that extend generally upwardly from the base portion 166 a predetermined length. Preferably, the tabs 165 are radially spaced apart from and generally surround the holder attachment 170, with each such tab 165 preferably positioned generally intermediate each adjacent pair of holes 167, 168 and 169, such that a suture may conveniently be positioned between the holder attachment 170 and a respective tab 165, shown as phantom lines 177 in FIG. 8.

The annular ring 164 of the holder 160 includes two sides, with the lower side preferably dimensioned and configured for engaging the inflow base portion 131 of a valve prosthesis 120 and may be secured to the valve prosthesis 120 by appropriate suturing through the plurality of holes 167, 168, and 169. Preferably, three individual sutures, each having first and second ends, are used to secure the valve holder 160 to inflow end 131 of the heart valve prosthesis 120. It will be understood and appreciated that while the prosthesis 120 illustrated in FIG. 9 is a preferred natural tissue valve prosthesis appropriately configured for mitral valve replacement, such as described with respect to FIGS. 4 and 5, the holder 160 may conveniently be adapted to implant substantially any heart valve prosthesis, although preferably to replace a mitral valve. With the valve 120, for example, lower side 173 of holder 160 engages the inflow end 131 of valve 120, with the axis of the holder generally aligned with the axis of the valve and each commissure post 142, 144 and 146 generally aligned with a respective spoke 161, 163 and 162 of the holder proximal said holes 167, 168 and 169, respectively. Each post 142, 144 and 146 includes a post tip 143, 145 and 147 distal the inflow end 131. A suture 104 extends through one hole 167 of the holder 160 and extends down the length of the respective post 142, through the implantation flange 128 adjacent the post exterior surface and through the post tip 143, suitably through the pericardium strip 132 covering the tip 143. The suture 104 then extends across to an adjacent post tip, suitably tip 147 of post 146, through the tip 147, suitably through the pericardium 132 that covers tip 147, and then extends generally along the exterior of post 146 through the implantation flange 128 to the hole 168 of the valve holder 160, where it is appropriately secured, such as by tying, to the other end of suture 104 to provide an appropriate amount of tension in the suture 104. In a similar manner, two additional sutures may secure the valve holder 160 to the valve prosthesis 120 by connecting between the holes 168 and 169 and the holes 169 and 167. These additional sutures 105 and 106 extend, for example, from a respective hole 168 or 169, down the length of the post 146 or 144, through the implantation flange 128, through the pericardium strip 132 covering the post tip 147 or 145, over to on adjacent tip 145 or 143, through the pericardium 132 covering the respective tip 145 or 143, extend upward along the post 144 or 142 and through the implantation flange 128 to a respective hole 169 or 167. The two ends of the respective sutures 105 and 106, that extend through holes 167 and 169, and 168 and 169, respectively, are tied off, maintaining an appropriate amount of tension in each suture 105 and 106. When viewed from the outflow side of the valve 120, the sutures 104, 105 and 106 are in place, they collectively form a generally triangular shaped suture, generally indicated as 110, connecting between the three post tips 143, 145 and 147, shown in FIGS. 8 and 9.

Prior to implantation of the valve prosthesis 120, each suture extending between each pair of respective spokes are generally moveable in that they may provide traction to the posts 142, 144 and 146 by positioning the respective sutures 104, 105 and 106 between a proximal respective suture tab 165 and the holder attachment 170, shown by phantom lines 177, to a position of engagement with the respective proximal tabs 165. The tractioning of each suture 104, 105 and 106 with the tabs 165 generally urges the pair of adjacent posts through which each such suture extends generally inwardly toward the central axis of the valve prosthesis 120. This substantially reduces "looping" of the posts 142, 144, and 146 with the surgeons implant stitches during the implantation procedure. The valve prosthesis 120 and valve holder 160 combination shown in FIG. 8 is generally positioned within a patient's atrioventricular orifice by a substantially elongated tool 175 that may be connected to the holder attachment 170 of the valve holder 160. Preferably, the elongated shaft 174 of tool 175 is made of a substantially lightweight and flexible alloy material or the like, and may be discarded after the implant procedure. In addition, because of the convenient attachment of the holder 160 to the valve heart prosthesis 120, the atrioventricular valve holder 160 as well as the attachment tool 175 illustrated in FIGS. 7, 8 and 9 may remain attached to the mitral valve prosthesis 120 during a substantial portion of the implantation procedure, suitably until the implantation flange 128 has been anchored appropriately to the patient's atrioventricular orifice. Once the valve prosthesis 120 has been anchored to the orifice, the sutures 104, 105 and 106 may be easily removed, suitably by severing each structure, along with the valve holder 160. Allowing the valve holder 160 and attachment tool 175 to remain attached to the valve prosthesis 120 during the implantation procedure greatly facilitates the implantation of the mitral replacement valve.

Figure 11:
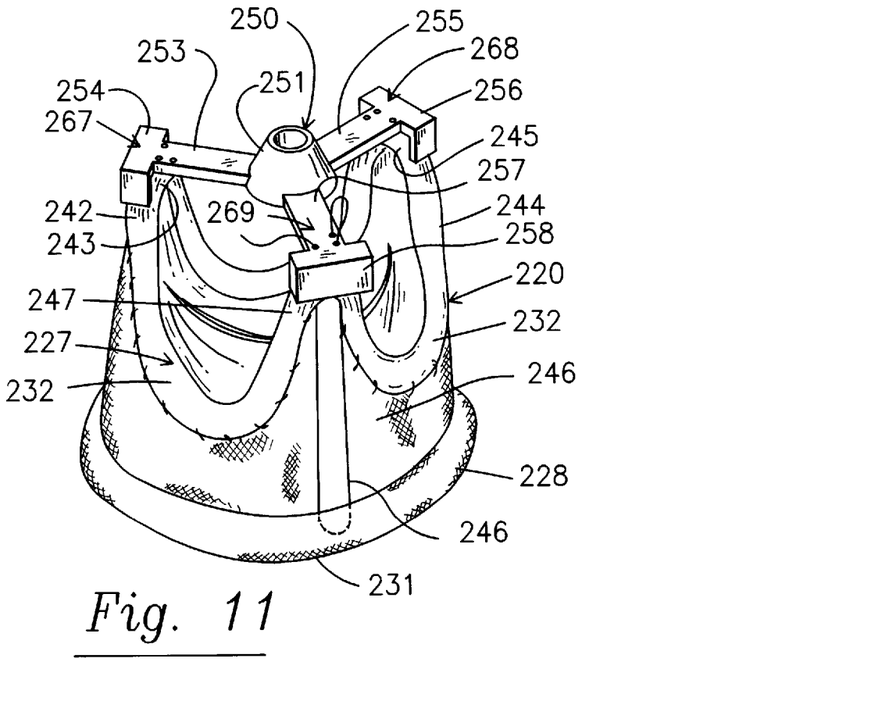
FIG. 11 is a perspective view of a preferred embodiment of the valve holder of FIG. 10 attached to a heart valve prosthesis in accordance with the present invention.
Figure 12:
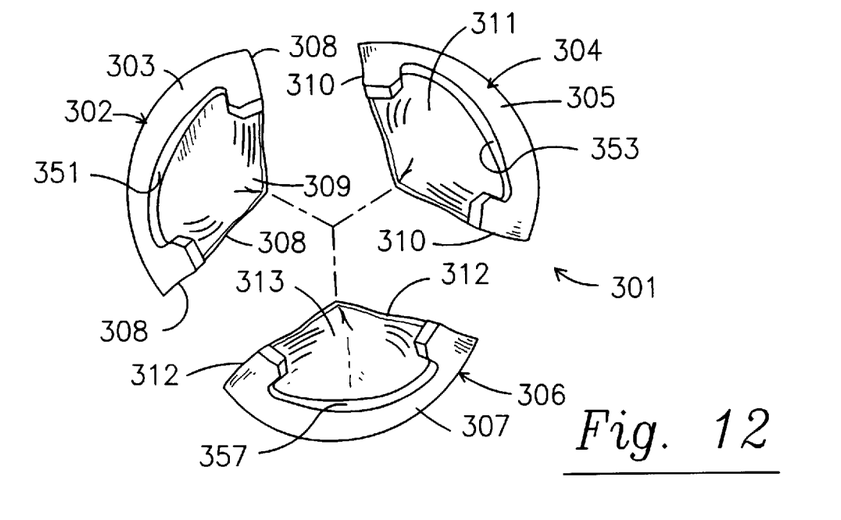
FIG. 12 is an exploded view of a preferred embodiment of a tri-composite heart valve in accordance with the present invention.

Referring to FIGS. 10 and 11, where the reference numbers of corresponding components of the heart valve prosthesis of FIG. 4 have been increased by adding 200, an aortic valve holder, generally indicated as 250, may be attached to an aortic heart valve prosthesis 220. The valve holder 250 preferably includes an axial base portion 251 with three arms 253, 255 and 257 spaced apart and extending from the base 251 and configured for attachment to a heart valve prosthesis 220. However, rather than attaching to the inflow side as the atrioventricular valve holder in FIG. 7, the aortic holder 250 may be attached, such as by suture, at the outflow side of the heart valve prosthesis 220. Preferably, the post tips 243, 245 and 247 of the prosthesis fit into and engage the respective receptacles 254, 256, and 258 of the valve holder 250, shown in FIG. 11. In order to facilitate the suturing between the holder 250 and the valve prosthesis 220, a plurality of holes 267, 268 and 269 preferably extend through each arm 253, 255 and 257 proximal the respective receptacles 254, 256 and 258. In this manner, three simple sutures may secure the holder 250 to the valve 214, with each suture preferably passing through a respective one of the plurality of holes 267, 268 and 269, extending through the pericardium 232 covering the tips 243, 245 and 247 of the aortic heart valve prosthesis 220, extending to and anchoring in the implantation flange 228. Each suture then may extend along a respective stent post 242, 244 and 246, pass through the pericardium strip 232, extend through a respective one of the plurality of holes 267, 268 and 269 and be appropriately tied off. The valve holder 250 generally provides passive support to the tips 243, 245 and 247 and may be attached to an appropriate attachment tool, similar to that described with respect to the embodiment of FIG. 8.

FIGS. 12 through 17 are directed to alternative preferred embodiments of the present invention that generally include a composite cardiac valve prosthesis having three leaflets 302, 304 and 306, each preferably being the non-coronary leaflet of a porcine aortic heart valve. Such non-coronary leaflets are obtained preferably from porcine aortic valves that have undergone an appropriate fixation process, such as described above with respect to FIG. 2. The non-coronary leaflets, as opposed to coronary leaflets, generally enhance the durability of the composite valve because of the fibrous attachment of each cusp to its respective valve wall. Once the porcine valves have undergone the appropriate fixation process, each prospective leaflet may be excised from an appropriate porcine valve for inclusion in the valve prostheses illustrated in FIGS. 12 through 17. These excised leaflets, generally indicated as 302, 304 and 306, are carefully examined and matched with leaflets of similar size, shape and symmetry, shown in FIG. 12, and may be temporarily attached to each other, such as by suture, in order to ensure that the three leaflets are suitable matches to form a substantially symmetrical tri-composite valve. Matching the leaflets in this manner generally provides an improved operation of the composite valve, including substantially simultaneous opening and closing of the valve leaflets, and, consequently enhanced hemodynamics and efficiency of the valve 301. Each such leaflet suitably includes a valve wall 303, 305 and 307 and a cusp 309, 311 and 313, with each valve wall 303, 305 and 307 further including a pair of generally opposed side edges 308, 310 and 312, an inflow edge and an outflow edge. Each cusp 309, 311 and 313 is attached to and extends from its respective valve wall 303, 305 and 307 proximal its inflow edge, suitably integral with the valve wall 303, 305 and 307. The outflow edge of each leaflet preferably has at least a substantial portion of excess valve wall tissue removed generally along the attachment of each cusp and its respective valve wall 303, 305 and 307 to form a sinus 351, 353 and 357 between the side edges of each valve wall. It is preferable that substantially little, if any, free margin remains beyond such attachment.

Figure 13:
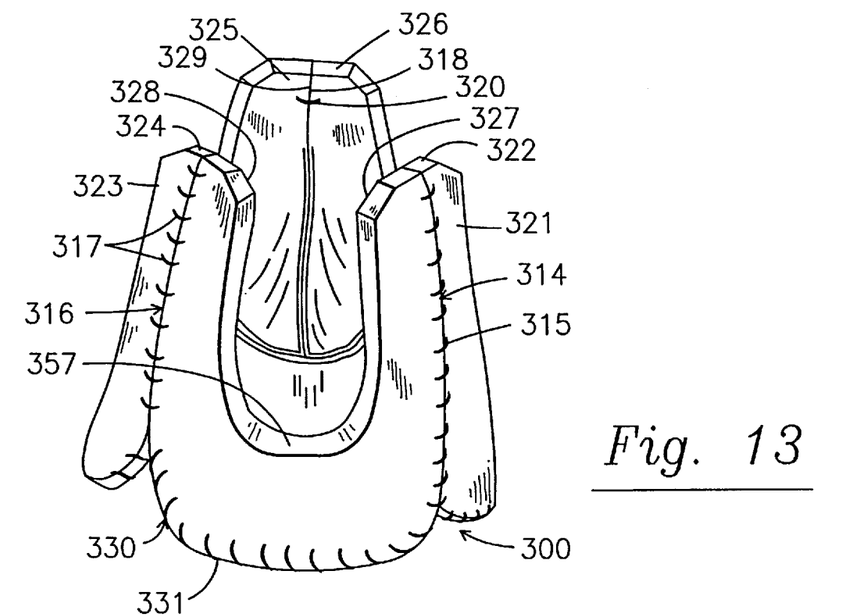
FIG. 13 is a perspective view of a preferred embodiment of a tri-composite heart valve in accordance with the present invention.

The tanned leaflets 302, 304 and 306 are selected to be suitable for inclusion in a heart valve prosthesis and are assembled to form a tri-composite valve 301 such as that illustrated in FIG. 13. The leaflets are preferably stitched at their respectively adjacent cut side edges 308, 310 and 312 along the outside surface behind each commissure 314, 316 and 318 between the respective leaflets 302, 304 and 306, such as by a continuous ladder stitch 315 and 317, with the attachment between the valve walls of adjacent leaflets defining each commissure post 321, 323 and 325 between each leaflet sinus 351, 353 and 357. A single stitch 320 may be exposed on the internal side of the valve 301 along each commissure 314, 316 and 338 proximal the top edge 322, 324 and 326 of each commissure post 321, 323 and 325, respectively. A continuous stitch may be placed around the inflow end of the base portion 330 of the composite valve to inhibit delamination of the valve. In addition, as illustrated in the preferred embodiment of FIG. 13, the top edges 322, 324 and 326 of each commissure post 321, 323 and 325, respectively, preferably are cut substantially flat just above a top commissure stitch with the sides of each post proximal the top edges cut at an appropriate angle. Of course, the top edges 322, 324 and 326 of each respective commissure post 321, 323 and 325 may be substantially curved or flat rather than be substantially flat with such angled corners.

The tri-composite valve 301 should be assembled such that there is substantial coaptation, or generally axial engagement, between each of the cusps 309, 311 and 313, which preferably ranges between about 2 mm and about 4 mm, or approximately 50% of the cusp surfaces when the valve is in its closed position. This preferred leaflet coaptation may be enhanced during the fixation process as described above as well as by the selecting of substantially symmetrical leaflets for inclusion in the heart valve 301. The difference in length between each adjacent free margin 327, 328 and 329 is preferably less than about 3 mm, depending generally upon the size of the tri-composite heart valve 301. In addition, it is preferable that substantially little, generally less than about 3 mm, if any, valve wall extends beyond the attachment of each cusp 309, 311 and 313 and its respective valve wall at the outflow end of the composite valve 301. Accordingly, the tri-composite heart valve 301 is similar to the porcine heart valve shown in FIG. 3, and will often experience improved performance over conventional non-composite valves because of the desired level of coaptation resulting from the selection and assembly of the individual and generally same size, symmetrical leaflets.

Figure 14:
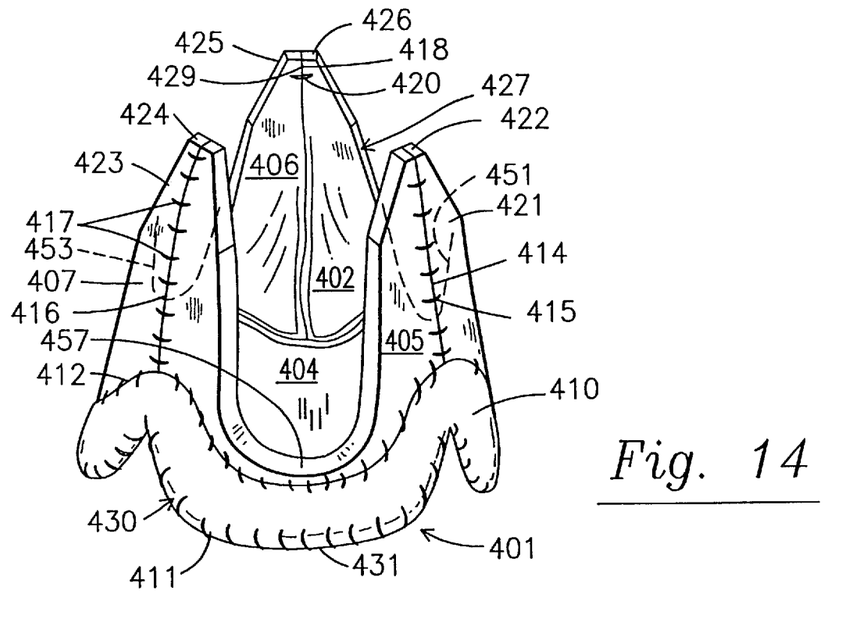
FIG. 14 is a perspective view of a preferred embodiment of an unstented tri-composite heart valve prosthesis in accordance with the present invention.

The tri-composite valve 301 may be mounted in an appropriate anatomical stent, typically ranging in thickness from zero to about 1 mm, with zero referring to an unstented heart valve 301. A preferred embodiment of the unstented heart valve is shown in FIG. 14 in which, for simplicity of illustration, similar reference numbers increased by adding 100 indicate corresponding components of the valve of FIG. 13. In order to facilitate the implantation of an unstented heart valve prosthesis 401, a pericardial bias 410 may be secured to the exterior surface proximal the base 430 of the unstented, tri-composite heart valve prosthesis 401 to provide support to the unstented heart valve 401 as well as provide additional structure that may be sutured to, or positioned proximal, an appropriate valve orifice.

Preferably, the bias 410 includes a pair of side edges that are dimensioned and configured to substantially conform to the inflow and outflow ends of the base portion 430 of the unstented valve prosthesis 401. A pericardium bias 410 generally will not abrade the valve leaflets or the patient's valve orifice as may the textile material covering many conventional prostheses. In addition to the inclusion pericardium bias 410, the valve wall tissue is preferably trimmed from the valve leaflets 402, 404 and 406 beyond the attachment of each cusp 409, 411 and 413 and its respective valve wall 403, 405 and 407 to form substantially narrow commissure posts 421, 423, and 425 that are substantially free of excess valve wall tissue along their respective side edges. This preferably includes removing excess valve wall tissue from each leaflet outflow end intermediate each commissure post 421, 423, and 425 to further enlarge and define each sinus 451, 453 and 457 formed between adjacent posts 421, 423 and 425. In addition, as is further shown in FIG. 14, this also preferably includes further trimming the valve wall tissue proximal the top edges 422, 424 and 426 of each respective commissure post 421, 423 and 425 at angles that may be substantially greater than that of the tri-composite valve illustrated in FIG. 13 such that the side edges of each post 421, 423, and 425 taper, or decrease in distance, toward the generally flat top edges 422, 424 and 426. The narrower posts and steeper angles of the top edges 422, 424 and 426 of the respective commissure posts and the pericardial bias 410 generally facilitate the implantation of the unstented heart valve prosthesis 401, as well as provide for increased flexibility and durability of the valve prosthesis. In addition, removing such valve wall tissue also permits a larger valve with a larger flow orifice to be used for a given patient, thereby increasing the available operative hydraulic performance of the valve prosthesis. While the unstented heart valve prosthesis 401 may require a greater degree of surgical proficiency to implant, it generally is more compatible with human recipients as it comprises virtually only tanned natural pericardial tissue, except for its sutures.

The stent 319 in which the tri-composite heart valve 301 illustrated in FIG. 13 may be mounted is substantially identical in construction to those utilized in conjunction with the heart valve embodiment illustrated in FIG. 4 but are preferably less rigid. The stents are formed of a resilient material, suitably Delrin, with a generally cylindrical sidewall portion having a generally uniform sidewall thickness of less than about 1 mm. Depending on the desired rigidity of the stents, its sidewall portion may vary in thickness, preferably ranging from about 0.25 mm to about 1.00 mm. By decreasing the thickness of the stent 319, the stent 319 will be more flexible and, consequently, the resulting heart valve prosthesis, which is formed by mounting a valve therein, will more closely approximate a natural heart valve when implanted. A thinner stent sidewall also enables a heart valve having a greater inner diameter and greater outer diameter to be mounted within a stent, having a given outer diameter, thereby improving the hemodynamics of the resulting heart valve prosthesis. In addition, because the tri-composite valve 301 is substantially symmetrical, the stent in which it is to be mounted should also be substantially symmetrical. Thus, the tri-composite heart valve 301 is preferably mounted to an appropriately sized and shaped Dacron-covered, symmetrical stent 319 such as by suturing the exterior of the valve 301 to the Dacron covering 331. Such sutures may include about three spaced apart stitches along the exterior of each commissure 314, 316 and 318 and sutures along the annular base portion 330 that further inhibit delamination of the valve 301. Preferably no stitches from mounting valve 301 to the stent 319 are exposed on the internal side of the valve 301. Of course other stitching configurations may be used with equal facility. In addition, each commissure post 321, 323 and 325 is suitably dimensioned and configured to generally correspond to the posts of the stent in which the valve 301 is to be mounted.

Figure 15:
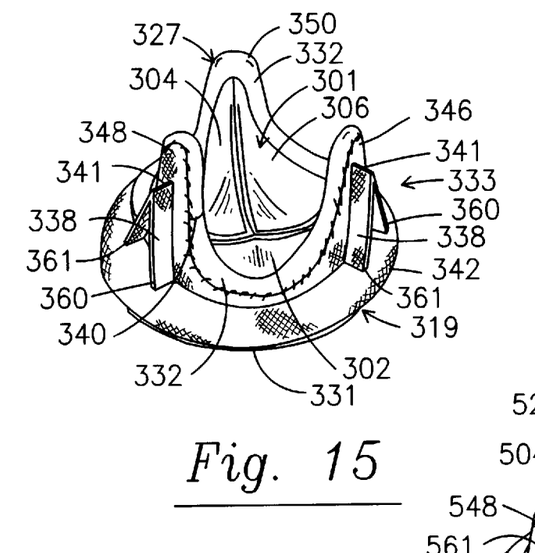
FIG. 15 is an outflow perspective view of a preferred embodiment of a stented, tri-composite aortic heart valve prosthesis in accordance with the present invention.
Figure 16:
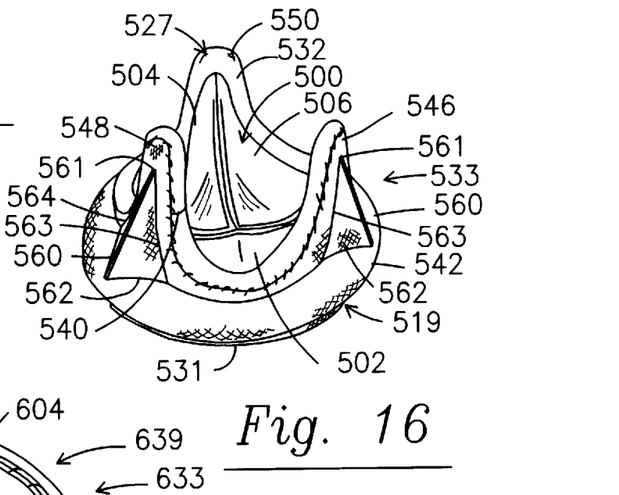
FIG. 16 is an outflow perspective view of a preferred embodiment of a stented, tri-composite mitral heart valve prosthesis in accordance with the present invention.

As shown in FIGS. 15 and 16, an appropriate tissue strip 332, which may suitably be equine or porcine pericardium, is attached to at least a portion of the outflow rail 335, preferably the entire outflow rail 335, of the stented, tri-composite valve 333, preferably with the visceral side of the pericardium strip 332 being exposed. The butt seam 340 of the pericardium strip 332 is preferably positioned along the side of one of the commissure posts intermediate the tip and the base portion of a post as shown in FIGS. 15 and 16. Preferably, the two ends of the pericardium strip 332 are seamed together end to end at seam 340 with no overlap and are affixed to the prosthesis 333 with no stitches being exposed to the valve leaflets 302, 304 and 306. Accordingly, the pericardium strip 332 may inhibit the abrasions that might otherwise result from the leaflets 302, 304 and 306 engaging the Dacron covering 331 of the stent structure. A relatively small composite valve may not have pericardial covering but, rather, a continuous aortic margin stitch may be employed to secure the aortic wall of the tri-composite valve to the outflow stent rails (not shown).

FIGS. 15 and 16 illustrate an embodiment of the present invention where the heart valve is mounted within a relatively thin stent 319, having a sidewall thickness of less than about 1 mm, in which a support is attached to the exterior of each stent post and to the implantation flange 342. FIG. 15 illustrates a prosthesis generally configured for aortic valve replacement with a V-shaped support 338, suitably formed of a textile material such as commercially available Dacron. Each V-shaped support has first and second ends 360 and 361 positioned distal from an apex 341, with the apex 341 attached proximal the tip of each respective stent post 346, 348 and 350. The first and second ends 360 and 361 of each V-shaped support 338 are attached to the flange on the opposing sides of the apex, with the width of each V-shaped support 338 typically ranging between about 1.3 mm and about 3.0 mm, generally less than or equal to the width of the implantation flange, oriented substantially transverse to each stent post 346, 348 and 350.

FIG. 16 illustrates a preferred embodiment of a tri-composite heart valve prosthesis configured for mitral valve replacement mounted in a relatively thin stent 519. Similar reference numbers, increased by adding 200, refer to parallel elements shown in FIG. 15. The stent 519 includes a support similar to FIG. 15, but with a support web 560 of a cloth material, which may suitably be Dacron, attached to the exterior of each stent post 546, 548 and 550 in order to provide additional support to each stent post 546, 548 and 550. The support web 560 may suitably be formed by folding the cloth generally in half to form a sail-like web that may be anchored, such as by suture, along each stent post with its fold aligned generally with the commissure between each of the three leaflets. Each support web includes a generally V-shaped base portion 562, an apex 561 and a pair of generally opposed side edges extending between the apex 561 and the base portion 562. The center portion of base 562 is attached to the outflow side of the implantation flange 542 radially outwardly from each respective post, with the distance between the side edges at a maximum adjacent the respective commissure post 548, 546 or 550 and flange 542. At least a portion of the side edges 563 and 564 of the web 560 engage, or preferably are attached to, the exterior of a respective commissure post 546, 548 and 550 with the distance between opposing side edges 563 and 564 decreasing in distance from the implantation flange 542 toward the apex 561. Preferably, the apex is attached proximal the tip of a respective post 546, 548 and 550. Accordingly, during the implantation procedure each support web 560 may suitably be anchored to a patient's atrioventricular orifice or surrounding tissue to reinforce the stent post 546, 548 and 550 and inhibit their inward deflection. It will be understood and appreciated that each of the supports illustrated in FIGS. 15 and 16 are equally applicable to prostheses configured for mitral or aortic valve replacement.

Figure 17:
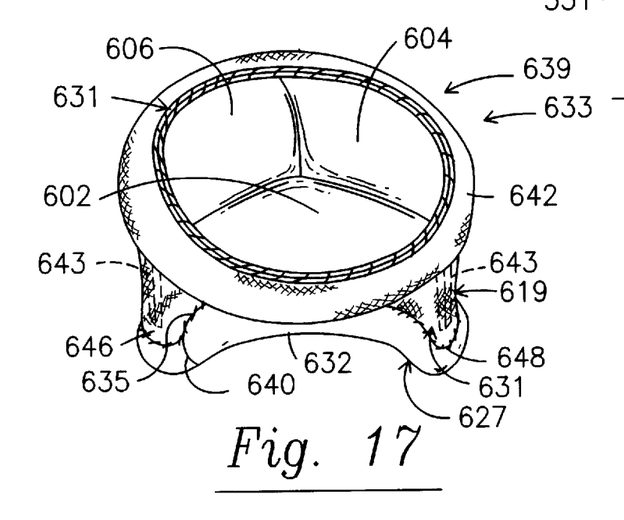
FIG. 17 is an outflow perspective view of a preferred embodiment of a stented, tri-composite heart valve prosthesis with radio-opaque markers positioned on each stent in accordance with the present invention.

As illustrated in the preferred embodiment of FIG. 17, radio-opaque markers 643 in the shape of thin strips may be positioned along each stent post. Similar reference numbers, increased by adding 300, refer to corresponding elements shown in FIG. 15. Preferably, such radio-opaque markers 643 are positioned substantially longitudinally along the exterior of each elongated stent post 646 and 648 beneath the Dacron covering. By moving the radio-opaque markers 643 from the implantation flange 642, to the stent posts, as discussed with respect to FIG. 4, the overall flow rate of the heart valve orifice may be improved as a result of the increase in the inner diameter to outer diameter ratio of the heart valve prosthesis 633. This typically allows the physician to utilize a valve prosthesis that has a larger flow orifice than most conventional valves of comparable size. Such radio-opaque markers 643 may also be used in conjunction with the supports of FIGS. 15 and 16, suitably positioned intermediate the two legs of the V-shaped support 338 of FIG. 15 beneath the Dacron covering of the stent 319 or between the side edges of web 560 beneath the Dacron covering of stent 519. FIG. 17 also illustrates the preferred symmetry of the leaflet cusps 602, 604 and 606, and is illustrated in the context of a valve prosthesis 633 configured for aortic valve replacement with the implantation flange 642 positioned adjacent the inflow end 631 of the prosthesis 633.

Figure 6:
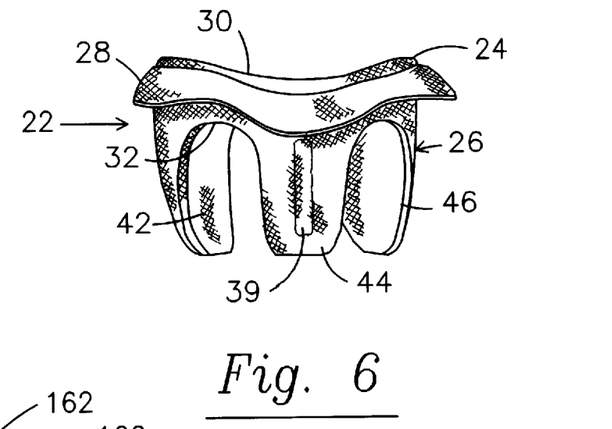
FIG. 6 is a side elevation of a preferred embodiment of a stent configured for an aortic heart valve prosthesis in accordance with the present invention.

In order to facilitate the implantation of the stented, tri-composite valve prosthesis 333, the position of the implantation flange 342 on the tri-composite, stented heart valve prosthesis may vary as discussed with respect to the alternative preferred embodiment of FIG. 4, and the positioning of the flange 342 with respect to the inflow end, and may even be more pronounced. Thus, where the valve prosthesis 333 is an aortic replacement valve, the implantation flange 342 is positioned preferably substantially adjacent to the inflow edge 344 of valve 301, similar as shown in FIG. 5. In contrast, the implantation flange 342 for mitral valve preferably is positioned adjacent the outflow or aortic end, such as illustrated in FIG. 6.

In order to further facilitate the implantation of the stented, tri-composite valve prosthesis 333 and 533 shown in FIGS. 15 and 16, respectively, appropriate valve holders may be attached to the inflow or outflow edge of the valve prosthesis. The valve holders and the attachment of each valve prosthesis to the respective holders are substantially identical to those shown and described with respect to the preferred embodiments of FIGS. 7 through 11, other than the radial placement of the spokes of such holders being substantially symmetrical to correspond to the configuration of the valve prosthesis. The preferred valve holder configuration and the attachment of the valve holder to the valve prosthesis generally depends upon whether the valve prosthesis is an aortic valve prosthesis or a mitral valve prosthesis. The post tips 343, 345 and 347 of an aortic replacement valve prosthesis 333 preferably may fit snugly into and be sutured to the respective receptacles 254, 256 and 258 of the valve holder 250, substantially as shown and described with respect to FIGS. 10 and 11. As stated above, the aortic valve holder 250 provides a substantially passive support to the valve prosthesis 333 during implantation.

Similarly, a substantially symmetrical mitral valve holder similar to that illustrated in FIGS. 7, 8 and 9 may likewise be secured to the inflow edge 539 of a heart valve prosthesis, such as the tri-composite, stented valve prosthesis 533 that has been configured appropriately for mitral valve replacement, similar to as shown in FIG. 8. Preferably, as described with respect to FIGS. 8 and 9, three sutures 104, 105 and 106 collectively form a triangle shape suture 110 between the three stent post tips 143, 145 and 147. Tension may be applied to the sutures 104, 105 and 106 prior to implantation such that the posts 142, 144 and 146 of the valve will bend slightly inwardly above the valve holder 160 to inhibit "looping" of the posts with a surgeon's implant stitches. As stated above, this may be accomplished by positioning each suture 104, 105 and 106 generally around the respective proximal suture tabs 165 substantially as shown and described with respect to FIG. 8.

Numerous variations in modifications of the present invention, all within the scope of this invention, will readily occur to those skilled in the art. All such modifications and variations are considered to be fully within the scope of this invention and the forgoing detailed description is to be considered illustrative only of the principles of this invention and not limitive thereof. The scope of the present invention is to be determined solely by the claims appended hereto.

What is claimed is:

1. A heart valve prosthesis comprising:
   three adjacent tanned heart valve leaflets of generally similar size, shape and symmetry, each said valve leaflet including a valve wall and a cusp, each said leaflet valve wall having an inflow end, and outflow end and a pair of generally opposed side edges extending between said inflow and outflow ends, each leaflet cusp attached to and extending from said leaflet valve wall proximal said inflow end, each said leaflet being attached to an adjacent pair of said leaflets along at least a portion of a respectively adjacent said valve wall side edges such that there is substantial coaptation between said cusps; and
   a stent having an inflow end, an outflow end, an annular base portion proximal said stent inflow end, with an implantation flange attached to and circumscribing said stent base portion, and at least three generally elongated stent posts extending from said stent base in a generally parallel and spaced apart relation that generally corresponds to the position of said valve cusps, said stent having interior and exterior portions, and said composite valve is attached within said stent such that said inflow end of said valve is positioned adjacent said inflow end of said stent with said outflow end of said valve proximal said stent posts, said stent further comprising a resilient material having a generally uniform thickness of about 1 mm or less with each said post outflow end defining a tip, each of said stent post including an exterior; and
   a support attached to said exterior of at least one of said stent posts and to the exterior of said flange to inhibit inward deflection of said supported stent post.

2. A heart valve prosthesis as claimed in claim 1 further comprising a pericardial bias attached proximal said inflow edge of said composite valve.

3. A heart valve prosthesis as claimed in claim 1 wherein said support comprises a V-shaped support having first and second ends distal from an apex, said apex attached proximal said tip of a respective said stent post and said first and second ends being attached to said flange on opposing sides of said apex.

4. A heart valve prosthesis as claimed in claim 1 wherein said support comprises a web having a base, an apex and a pair of generally opposed side edges extending between said apex and said base, said base being attached to said flange and at least a portion of said side edges being attached to said exterior of a respective said stent post in spaced apart relation decreasing in distance toward said apex, with said apex being positioned proximal said tip of a respective said stent post.

5. A heart valve prosthesis as claimed in claim 1 further comprising a support attached to said exterior of each said stent post and to said flange.

6. A heart valve prosthesis as claimed in claim 1 wherein said support comprises a textile material.

7. A method of making a heart valve prosthesis comprising:
   excising a plurality of leaflets from at least one heart valve, each said leaflet including a valve wall and a cusp, each leaflet valve wall having a pair of generally opposed side edges an inflow edge and an outflow edge, each said cusp attached to and extending from a respective said valve wall proximal said inflow edge;
   attaching each said leaflet to an adjacent pair of said leaflets along the respective said valve wall side edges such that there is substantial coaptation between said leaflets, with each said attachment between respective said side edges of adjacent leaflets defining a commissure post distal said inflow end of said prosthesis;
   attaching said composite heart valve prosthesis within a stent having an inflow end, an outflow end, an annular base portion proximal said stent inflow end, a plurality of posts integral therewith that extend from said base in a generally parallel and spaced apart relation that generally corresponds to the circumferential positioning of said cusps, said stent further including a generally nonabsorbent textile material covering at least a portion thereof, such that said inflow end of said valve is positioned adjacent said inflow end of said stent with said outflow end of said valve proximal said outflow end of said stent, each said stent post includes an exterior portion; and
   attaching a support to said exterior portion of said at least one said stent post and to the exterior of said flange to inhibit inward deflection of said supported stent post.

8. A method of making a heart valve prosthesis as claimed in claim 7 further comprising the step of attaching a pericardium strip to at least a portion of said textile material at said outflow end of said prosthesis to inhibit abrasion between said cusps and said textile material covering said stent.

9. A natural tissue heart valve prosthesis comprising:
   a natural tissue heart valve having three leaflet cusps, with said valve having an inflow end and an outflow end;
   a stent having an inflow end, an outflow end, a generally annular base portion proximal said stent inflow end, with an implantation flange attached to and circumscribing said stent base portion, and at least three generally elongated stent posts extending from said stent base portion in a generally parallel and spaced apart relation that generally corresponds to the position of said valve cusps, each said stent post terminating in a stent post tip, said stent having interior and exterior portions and a sidewall thickness of less than about 1.0 mm, and said heart valve being attached within said stent, such that said valve inflow end is positioned adjacent said stent inflow end and said valve outflow end is positioned proximal said stent posts; and a support attached to said exterior of at least one of said stent posts and the exterior of said implantation flange to inhibit inward deflection of said at least one stent post.

10. A heart valve prosthesis as claimed in claim 9 further comprising:

a support attached to said exterior of each said stent post to inhibit inward deflection of said respective stent posts.

11. The heart valve prosthesis as claimed in claim 9, wherein said support comprises:

a V-shaped support having first and second ends distal from an apex, said apex attached proximal to one of said stent post tips and said first and second ends of said V-shaped support being attached to said flange on opposing sides of said apex.

12. A heart valve prosthesis as claimed in claim 9 wherein said support comprises a web having a base, an apex and a pair of generally opposed side edges extending between said apex and said base, said web base being attached to said flange and at least a portion of said side edges being attached to said exterior of said one stent post in spaced apart relation decreasing in distance toward said apex, with said apex being positioned proximal to said outflow end said one stent post.

13. A heart valve prosthesis as claimed in claim 9 wherein said support comprises a textile material.

14. A natural tissue heart valve prosthesis comprising:

a natural tissue heart valve having three leaflet cusps, with said valve having an inflow end and an outflow end;

a stent having an inflow end, an outflow end, a generally annular base portion proximal said stent inflow end, with an implantation flange attached to and circumscribing said stent base portion, and at least three generally elongated stent posts extending from said stent base portion in a generally parallel and spaced apart relation that generally corresponds to the position of said valve cusps, with each said stent post terminating a stent post tip, said stent having interior and exterior portions and a sidewall thickness of less than about 1.0 mm, and with said heart valve being attached within said stent, such that said valve inflow end is positioned adjacent said stent inflow end and said valve outflow end is positioned proximal said stent posts; and a support attached to said exterior of at least one of said stent posts to inhibit inward deflection of said at least one stent post, said support comprising a textile material.

\* \* \* \* \*

UNITED STATES PATENT AND TRADEMARK OFFICE
CERTIFICATE OF CORRECTION

PATENT NO. : 5,861,028
DATED : January 19, 1999
INVENTOR(S) : William W. Angell

It is certified that error appears in the above-indentified patent and that said Letters Patent is hereby corrected as shown below:

Cover page, after item [76], but before item [21] insert
--Assignee: Shelhigh, Inc., Millburn, NJ.--

Signed and Sealed this

Twenty-eighth Day of September, 1999

Attest:

Q. TODD DICKINSON

*Attesting Officer*

*Acting Commissioner of Patents and Trademarks*